United States Patent
Higgs et al.

(10) Patent No.: US 7,113,276 B1
(45) Date of Patent: Sep. 26, 2006

(54) MICRO DEFECTS IN SEMI-CONDUCTORS

(75) Inventors: Victor Higgs, Hemel Hempstead (GB); Ian Christopher Mayes, Hemel Hempstead (GB); Freddie Yun Heng Chin, Hemel Hempstead (GB); Michael Sweeney, Hemel Hempstead (GB)

(73) Assignee: ASTI Operating Company, Inc., Mountain View, CA (US)

( * ) Notice: Subject to any disclaimer, the term of this patent is extended or adjusted under 35 U.S.C. 154(b) by 0 days.

(21) Appl. No.: 09/254,521

(22) PCT Filed: Sep. 5, 1997

(86) PCT No.: PCT/GB97/02388

§ 371 (c)(1),
(2), (4) Date: Mar. 8, 1999

(87) PCT Pub. No.: WO98/11425

PCT Pub. Date: Mar. 19, 1998

(30) Foreign Application Priority Data

Sep. 10, 1996 (GB) .................................. 9618897.4

(51) Int. Cl.
  *G01J 3/30* (2006.01)
  *G01J 3/00* (2006.01)
  *H01L 21/00* (2006.01)
(52) U.S. Cl. .......................... 356/318; 438/7; 438/16; 250/458.1
(58) Field of Classification Search .. 356/237.1–237.5, 356/318, 417, 326; 250/559.46, 559.09, 250/559.16, 458.1; 382/149, 147; 438/694, 438/8, 14
See application file for complete search history.

(56) References Cited

U.S. PATENT DOCUMENTS

| | | | | |
|---|---|---|---|---|
| 4,246,793 A | * | 1/1981 | Fairand et al. | ................. 73/628 |
| 6,075,592 A | * | 6/2000 | Banerjee et al. | ............ 356/318 |
| 6,429,968 B1 | * | 8/2002 | Carver | ........................ 359/385 |
| 6,911,347 B1 | * | 6/2005 | Higgs | ............................ 438/7 |
| 2004/0092042 A1 | * | 5/2004 | Higgs | .......................... 438/14 |

OTHER PUBLICATIONS

Bajaj et al., 1993, Semiconductor Science and Technology, 8:872-7.
Montangero et al., 1994, Materials Science and Engineering, B24:175-9.
Moore, 1990, J Crystal Growth, 103:21-7.
Pritchard et al., 1993, Semiconductor Science and Technology, 8:1166-72.
Ribes et al., 1995, Applied Physics Letters, 66:2321-3.

* cited by examiner

*Primary Examiner*—Hoa Q. Pham
(74) *Attorney, Agent, or Firm*—Perkins Coie, LLP

(57) ABSTRACT

The invention relates to a method and apparatus for detecting defects in a semiconductor or silicon structure at room temperature, and in an efficient time, using photoluminescence. The invention employs the use of a high intensity beam of light preferably having a spot size between 0.1 mm–0.5 microns and a peak or average power density of $10^4$–$10^9$ w/cm$^2$ with a view to generating a high concentration of charge carriers, which charge characters detect defects in a semiconductor by interacting with same. These defects are visible by producing a photoluminescence image of the semiconductor. Several wavelengths may be selected to identify defects at a selective depth as well as confocal optics may be used.

20 Claims, 5 Drawing Sheets

PL IMAGE OF AS-GROWN DEFECTS IN CZ Si
SCAN AREA 1mm x 1mm

PL IMAGE OF AS-GROWN DEFECTS IN CZ Si AFTER Fe CONTAMINATION $1 \times 10^{11}$ atoms.cm$^{-3}$
SCAN AREA 1mm x 1mm PL IMAGE OF OXYGEN PRECIPITATES IN ANNEALED Si
SCAN AREA 1mm x 1mm PL IMAGE OF Ni SILICIDE PRECIPITATES IN CMOS PROCESSED TEST WAFER
SCAN AREA 500 x 500 μm PL IMAGE OF Cu SILICIDE PRECIPITATES IN CMOS PROCESSED TEST WAFER
SCAN AREA 100mm x 100μm PL IMAGE OF Cu SILICIDE PRECIPITATES IN CMOS PROCESSED TEST WAFER,
a) HIGH INJECTION, b) LOW INJECTION.
SCAN AREA 37 x 39 μm MICROGRAPH OF LOCOS TEST STRUCTURE
SCAN AREA 120 x 60 μm PL IMAGE OF LOCOS TEST STRUCTURE REVEALING A HIGH DENSITY OF DISLOCATIONS
SCAN AREA 120 x 60 μm

MICRO DEFECTS IN SEMI-CONDUCTORS

BACKGROUND OF THE INVENTION

The invention relates to an apparatus and method for detecting micro defects in semiconductors or silicon and particularly, but not exclusively, in part-processed or bulk silicon.

Developments in crystal growth have enabled the production of silicon wafers free from dislocation. However, dislocation free wafers may not be able to remain this way after the wafers are subjected to high temperature processing. Defects formed within the device active region in the wafer and defects produced in the gate oxide generally degrade device performance, lead to yield losses and reliability problems. This invention can be used to locate and measure the electrical activity of these defects.

Transition metals, which are fast diffusers in silicon, readily form deep levels, ie away from the valance or conduction band edge, and also lead to decoration of both point and extended defects which eventually lead to device failure. These transition metal impurities also form recombination centres and traps which can dramatically reduce carrier lifetime and can also act as dark current generation sites, i.e. in the absence of light, charge leakage will occur. Gettering techniques, where mechanical damage, such as abrasion, is typically undertaken in order to provide a damaged site, which effectively acts as a sponge soaking up impurities in the wafer, have been developed to remove transition metal impurities from the device active areas. It therefore follows that the aforementioned damage is deliberately targeted to an area in the wafer remote from the electrical device. Thus internal gettering techniques introduce defects in the silicon substrate which attract unwanted impurities away from the device areas. Gettering sites need to be characterised to control their distribution for different process conditions, a task which can be performed with the present invention.

Epitaxial silicon, that is the deposited uppermost layers of silicon, typically in the order of microns thick, has been used to overcome problems with as-grown CZ wafers. In other words, as the thickness in the epitaxial silicon increases, given that this layer can be grown in a defect-free manner, it can be used as a site for the electric device without fear of contamination in the bulk wafer affecting the activity of the device. However it is not always possible to use an epitaxial layer of sufficient thickness for this activity and where the epitaxial layer is thin then defects in the bulk wafer can interfere with the electrical device. Moreover, epitaxial layers suffer from problems of metal contamination.

Several techniques already exist for the detection of defects in as-grown material, these include wet chemical etching in order to reveal flow pattern defects; light scattering topography where the topography of the surface wafer is examined using light to detect undulations which in turn are indicative of defects in the sub-structure; and transmission interference contrast microscopy where the transmission of light through the wafer is examined and the phase shift due to small path changes is used to image defects in the wafer. All of these techniques are used to measure the physical presence of defects in the wafer. However they do not measure the electrical properties of the defects and moreover in some cases they are destructive. Accordingly, as techniques for determining the structural integrity of a wafer they are lacking in terms of the information they provide and moreover they can be positively destructive. Photoluminescence (PL) spectroscopy is a very sensitive technique for investigating both intrinsic and extrinsic electronic transitions at impurities and defects in semiconductors. When silicon is excited at low temperatures with laser irradiation above the band-gap of the material, electron hole pairs are produced. These carriers can recombine in various different ways, some of which give rise to luminescence. The electron hole pairs formed at low temperature can be trapped at impurities in silicon and they emit photons characteristic of this interaction, thereby giving impurity specific information in the photoluminescence spectra. There are a significant number of applications of PL spectroscopy to silicon including characterisation of silicon after different processing steps, characteristic of device fabrication for example implantation, oxidation, plasma etching, the detection of point defect complexes and the presence of dislocations. One of the most important applications includes the non-destructive measurement of shallow donors and acceptors such as arsenic, boron and phosphorous. Notably, this technique enables the measurement of the concentration of these shallow doners and acceptors. However, in all these applications in order to obtain this spectral information and unambiguous chemical identification of the optical centres, measurements need to be carried out at liquid helium temperatures. It is known throughout the industry that at room temperature the PL signal is significantly weakened and very little useful spectral information can be obtained.

We are aware of one set of experiments only which describe use of PL spectroscopy at room temperature (Mapping of Micro Defects in Silicon Crystals by Photoluminescence at Room Temperature; Semiconductor Silicon 1990, Proceedings Volume 90–7, pages 994–1004). Although this paper demonstrates both deep-level PL and band-edge PL are detectable in silicon wafers at room temperature it is of note that the technique used involved obtaining spectral information and so spatial resolution was constrained and the time involved was high. This effectively limits the successful use of this technology. This is unfortunate because room temperature PL is ideal for non-destructive examination of the recombination properties of defects.

SUMMARY OF THE INVENTION

However, our investigations have lead us to develop a PL technique which has industrial application in that it enables the image to be produced within minutes. Moreover, our technique also has a further added advantage in that we are able to obtain a micro image of small individual defects near to the surface of the wafer; this is in contrast to the aforementioned PL room temperature technique which tends to produce a macro view of large defect clusters deep into the wafer.

Our technique can be described having regard to the following information.

The intensity of the PL intensity $I_{PL}$, as a function of the laser beam position (x,y), is given by:

$$I_{PL}(x,y) = k \int A R_{fn} \Delta n d^3 \quad (1)$$

Where k is the proportionality factor to allow for experimental parameters such as light collection efficiency, detector quantum efficiency. A and $R_r$ are correction factors for absorption losses, inside the material (A) and reflection losses at the surface ($R_r$). $\eta$ is the internal quantum efficiency of the semiconductor, $\Delta n$ is the excess carrier density and $d^3$ is the volume of material emitting light.

The defects alter the recombination properties of the carriers which is observed as a change in intensity in the PL image. We define the PL contrast C, as follows:

$$C(x, y) = \frac{I_{PL}(\infty) - I_{PL}(x, y)}{I_{PL}(\infty)} \quad (2)$$

where $I_{PL}(\infty)$ is the intensity far away from the defect, and $I_{PL}(x,y)$ at the position x,y.

When excess electron-hole pairs are produced in Si by above band gap excitation, recombination can either be radiative (emit light) or non radiative. The total recombination rate is expressed by the sum of two rates:

$$R = R_{rr} + R_{nr} \quad (3)$$

and the internal quantum efficiency, η of the semiconductor is given by:

$$\eta = \frac{R_{rr}}{R_{rr} + R_{nr}} \quad (4)$$

When the photoluminescence images are obtained any variations observed in the PL signal could be due to the spatial variations of both $R_{rr}$ and $R_{ir}$.

The recombination behaviour of the defect depends on the position of the levels in the band gap (deep or shallow) and on the carrier capture cross sections. At low injection levels the recombination rate is limited by the availability of the minority carriers, whereas at high injection levels, where the injected charge exceeds the equilibrium carrier concentration, the recombination rate is limited by the number of traps. Therefore increasing the injection level leads to enhanced recombination at the defect.

It is therefore an object of the invention to provide a photoluminescence technique which can be undertaken at room temperature and which provides information concerning defects in a semiconductor or silicon structure at a rate appropriate to industrial use and/or which enables us to visualise defects in the upper regions of the semiconductor or silicon structure and in particular near to the surface of same.

It is a further object of the invention to enhance non radiative recombination of electron hole pairs at defects in a semiconductor or silicon structure with a view to enhancing contrast in a PL image of said semiconductor or silicon structure so as to enhance the viewing of defects in same.

In its broadest aspect the invention is based on collecting luminescence from a semiconductor or silicon structure under selected excitation conditions the defects being observed due to a change in the carrier lifetime at the site of the defect.

We therefore use a high injection level laser in the method of the invention and defects are detected due to the local change in carrier lifetime at the defect. These defects are typically observed as darkened regions at the physical position of the defect, but in some instances enhanced radiative recombination gives rise to relatively lightened regions, having regard to the background.

The recombination at the defects is enhanced by increasing the injection level so that it is not limited by the availability of minority carriers.

We believe the success of our method is, in part, due to the probing volume of our laser being small (spatial resolution 0.1–20 μm, ideally 2–5 μm) and therefore localised defects have much greater effect on the measured PL intensity. We also believe our method is successful, in part, because since the excitation is focused the injected carrier density is high. This greatly increases the probability of non-radiated recombination at the defect and hence physical location of the defect.

According to a first aspect of the invention there is therefore provided a method for enhancing spatial and depth resolution in a semiconductor or silicon structure which method comprises exposing said semiconductor or silicon structure to a high-intensity laser and then determining the photoluminescence of same.

Ideally the method is undertaken for revealing defects in a semiconductor or silicon structure by improving the contrast and resolution.

Reference herein to a high-intensity laser is meant to include, without limitation, a high power density laser i.e. where regardless of the power of the laser the emittance is focused.

We have discovered that carrier diffusion lengths are greatly reduced under high injection laser conditions, the result of this is that the effective sampling depth is largely determined by the excitation laser penetration depth which is in turn determined by the wavelength of the excitation source. By using a short wavelength near surface defects can be examined. Conversely longer wavelengths can be used to look at defects deeper in the sample.

In a preferred method of the invention we use a pulsed laser excitation source and ideally measure the luminescence images as a function of time. This means that both depth and spatial resolution are improved and can be used to obtain information on the carrier capture cross sections of the defects. Time resolved measurements can also be used to measure the effective carrier lifetime and obtain lifetime maps.

In a further embodiment of the invention confocal optics are used to obtain depth discrimination of the defects by exciting a large volume of said semiconductor with a laser and collecting images from a series of focal planes.

According to a further aspect of the invention there is provided a method for identifying defects in a semiconductor or silicon structure comprising exposing said semiconductor or structure to at least one high intensity beam of light characterised by a spot size of between 0.1 mm–0.5 microns and a peak or average power of between $10^4$ to $10^9$ watts/$cm^2$; and collecting luminescence from the semiconductor or structure so as to observe defects in same.

Using either method of the invention it is possible to image defect distribution in part processed and bulk silicon. The method has application in determining defect distribution in all semiconductors and also for determining density and spacial distribution and measuring defect recombination of semiconductors.

According to a yet further aspect of the invention there is provided an apparatus for undertaking photoluminescence imaging of a semiconductor or silicon structure characterised in that it comprises a high intensity laser as herein described.

In a preferred embodiment of the invention said laser is modulatable so as to adjust the wavelength excitation of same thereby enabling a user of said apparatus to sample said semiconductor or silicon structure at different depths. For example, a short wavelength may be used to sample near the surface of the said semiconductor or structure and a longer wavelength to look deeper into the semiconductor or structure.

In yet a further preferred embodiment of the invention said apparatus is provided with means to enable pulsing of said laser and ideally also for PL images to be obtained as a function of time.

In a yet further preferred embodiment of the invention said apparatus is provided with means for modulating said laser at high frequencies (0.1–100 Mhz) thereby enabling a user of said apparatus to sample said semiconductor or silicon structure at different depths.

In yet a further preferred embodiment of the invention said apparatus comprises a laser of a spot size of between 0.1 mm and 0.5 microns and/or a power density of between $10^4$ to $10^9$ watts/cm$^2$.

In yet a further preferred embodiment of the invention said apparatus comprises confocal optics which is used to obtain depth discrimination of the defects by exciting a large volume of said semiconductor with a laser and collecting images from a series of focal planes.

BRIEF DESCRIPTION OF THE DRAWINGS

An embodiment of the invention will now be described, by way of example only, with reference to the following Figures wherein.

DETAILED DESCRIPTION OF THE INVENTION

Figure 1:
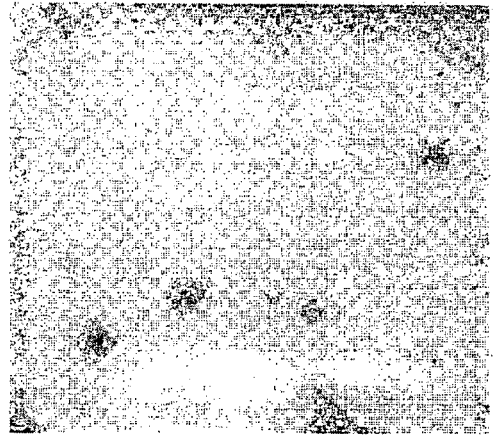
FIG. 1 is a PL image of as-grown defects in Czochralski (CZ) silicon, scan area 1 mm×1 mm using the apparatus of the invention.
Figure 2:
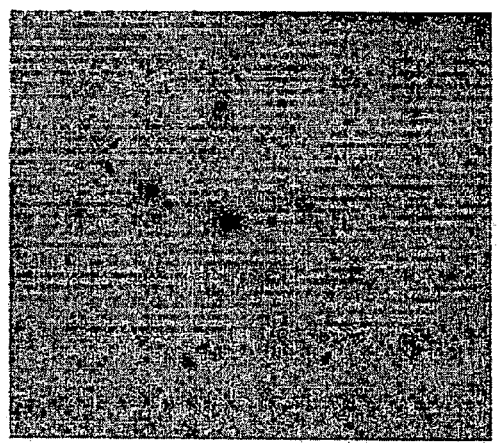
FIG. 2 is a PL image of as-grown defects in CZ silicon after iron contamination at $1\times10^{11}$ atoms.cm$^{-3}$, scan area 1 mm×1 mm using the apparatus of the invention.
Figure 3:
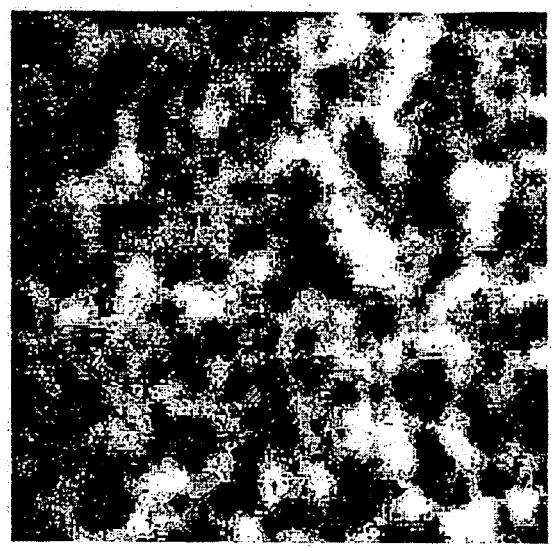
FIG. 3 is a PL image of oxygen precipitates in annealed silicon, scan area 1 mm×1 mm using the apparatus of the invention.
Figure 4:
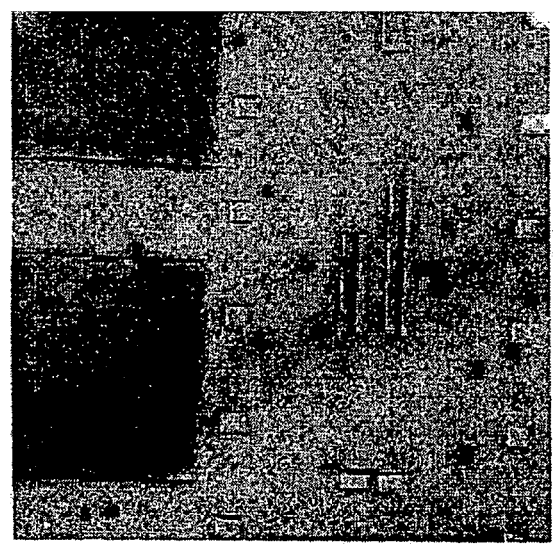
FIG. 4 is a PL image of nickel silicide precipitates in Complementary Metal Oxide Semiconductor (CMOS) processed test wafer, scan area 500 µm×500 µm using the apparatus of the invention.
Figure 5:
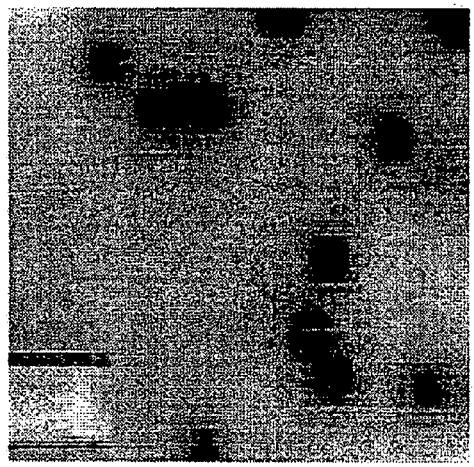
FIG. 5 is a PL image of copper silicide precipitates in CMOS processed test wafer, scan area 100 µm×100 µm using the apparatus of the invention.
Figure 6:
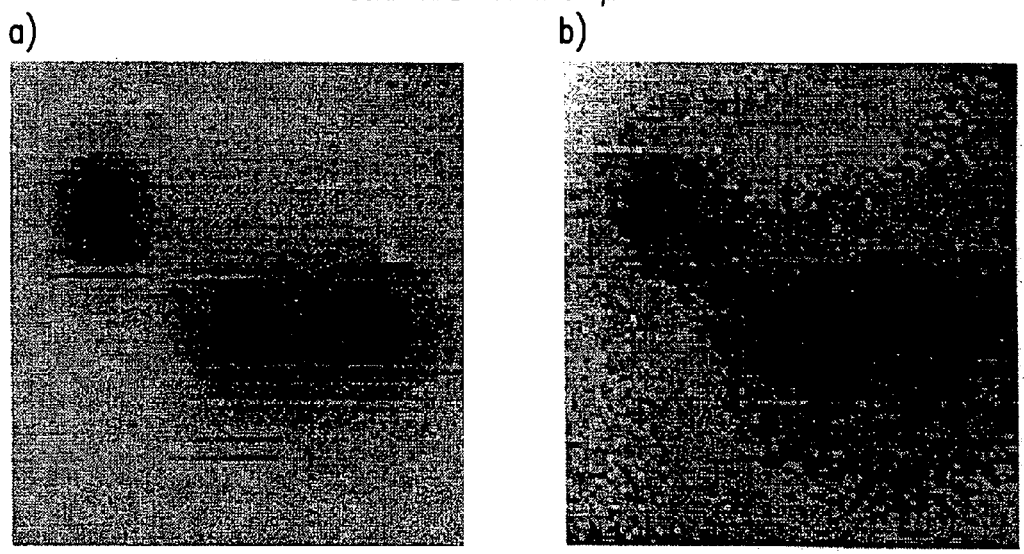
FIG. 6 is a PL image of copper silicide precipitates in CMOS processed test wafer, a) high injection, b) low injection, scan area 37 µm×39 µm.
Figure 7:
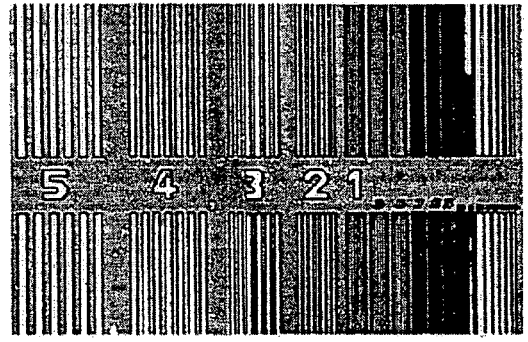
FIG. 7 is a micrograph of Local Oxidation of Silicon (LOCOS) test structure, scan area 120 µm×60 µm using the apparatus of the invention.
Figure 8:
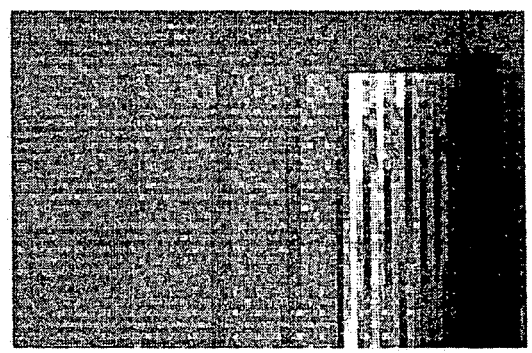
FIG. 8 is a PL image of LOCOS test structure revealing a high density of dislocation, scan area 120 µm×60 µm using the apparatus of the invention. The dark line on the right hand side of the image shows the region of high dislocation density.
Figure 9:
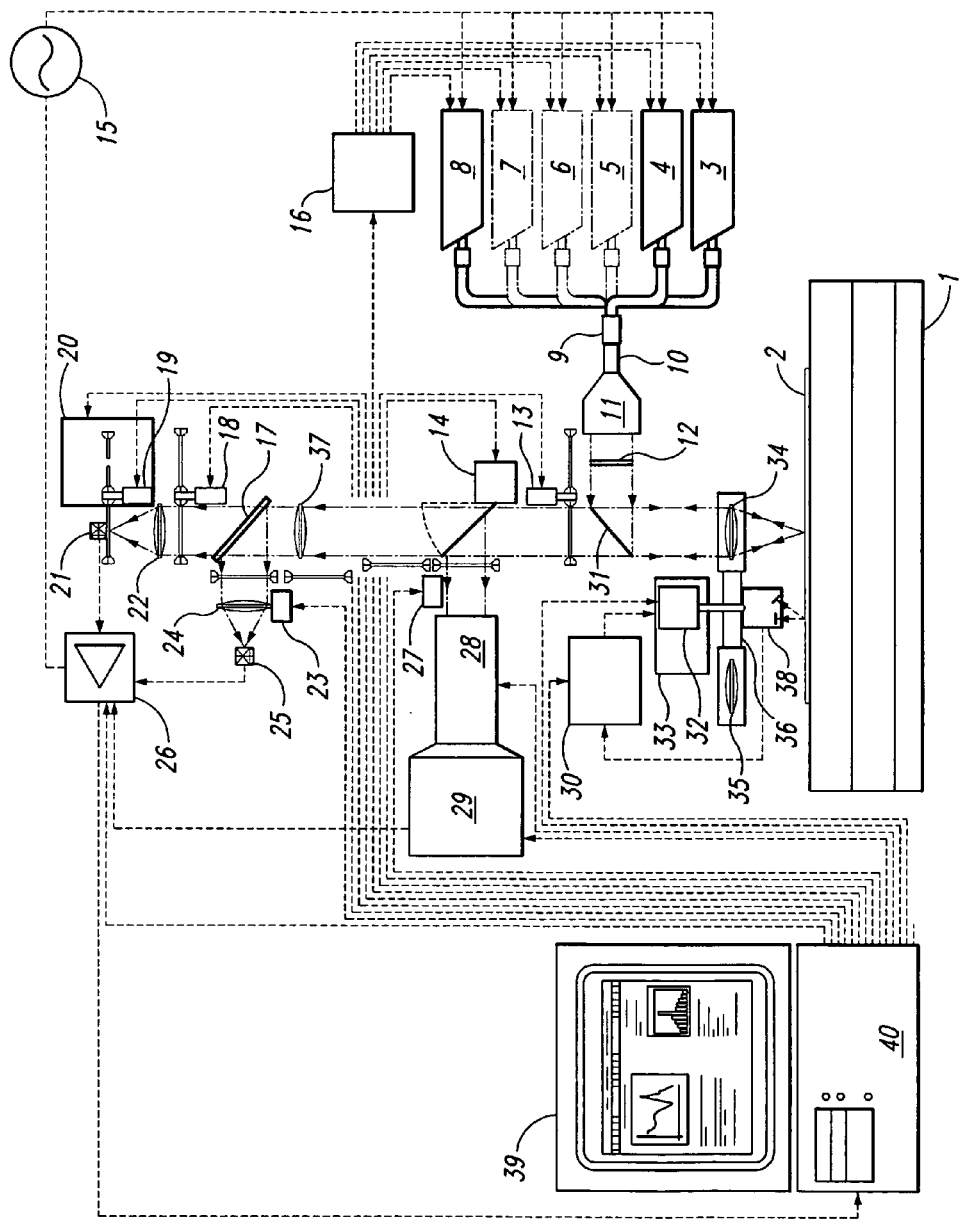
FIG. 9 is a diagrammatic illustration of an apparatus in accordance with the invention.

Referring to the figures and firstly to FIG. 9 there is shown a diagrammatic illustration of an apparatus in accordance with the invention.

The apparatus essentially comprises a PL imaging microscope which: towards the right hand side, comprises a bank of lasers 3–8; towards the bottom comprises a sample stage such as an X-Y table or R-Θ table; towards the left hand side comprises a microprocessor 40 and a display screen 39 and in the centre of the Figure there are shown various optical components for directing light through the system.

In the embodiment shown in FIG. 9, six lasers are provided with a view to probing different depths in the sample. However, it is within the scope of the invention to use only one laser, or indeed to use a greater number of lasers. In any event, at least one of the lasers is a high intensity laser and ideally has a spot size of between 0.1 mm and 0.5 micron and a power density of between $10^4$ to $10^9$ watts/cm$^2$. A laser selector 16 coupled with said bank of lasers is provided so as to select one or more lasers for use and further also to select the frequency and wavelength of the lasers.

Conventional optics, such as optical fibres 9 are used to direct light towards the collimater to 10 and laser beam expander 11. An apodization plate 12 is positioned between laser beam expander 11 and beam splitter 31. Beam splitter 31 directs a fraction of light from the aforementioned lasers towards sample 2 via objective 34.

An automatic focus controller 30 is provided and coupled to a piezo driven focusing stage 33. The microscope is equipped with a conventional rotating turret 36 which is provided with at least one high numerical aperture objective for micro examination and one low numerical aperture objective for macro examination 34,35 respectively. In addition, also coupled to turret 36 there is provided an optical displacement measuring system 38.

Cabling is provided so as to connect the automatic focusing controller 30 to microprocessor 40 and also a microscope objective indexing arrangement 32 to microprocessor 40.

Downstream of beam splitter 31 there is provided as filter wheel 13 for laser notch filters, down stream thereof there is provided a swing-aside folding mirror 14 whose function will be described hereinafter. Aligned with said mirror 14 there is provided a filter wheel 27 for wavelength selection, and rearward thereof there is provided a zoom lenses attached to a suitable CCD 2-D array detector 29.

Infinity system compensating lens 37 is provided in the optical path foremost of cold mirror 17 which reflects light towards a further filter wheel 23 for wavelength selection and a focusing lenses 24 which is foremost of a detector 25 for UV and visible light. Detector 25 is coupled to lock-in amplifier 26. This is used to obtain a reflected image of the surfaces.

Rearmost of cold mirror 17 is provided a further filter wheel 18 again for wavelength selection, and rearmost thereof a focusing lens 22 and a further aperture wheel 19 for pinhole selection which is provided foremost of a detector 21 for detecting the luminescence. Both the UV and visible region detector 25 and infrared detector 21 are coupled to lock-in amplifier 26.

Operation of the system is explained having regard to the following.

A range of wavelengths to probe different planes in the sample is provided by several lasers (3–8). The lasers can be modulated by a frequency generator (16) so that the signal emitted from the sample (2) can be isolated from background radiation by means of the detectors being synchronised to the laser modulation frequency by the lock-in amplifier (26). In a further embodiment, the range of wavelengths could be produced by using a tuneable laser and/or an Optical Parametric Oscillator. Each laser is connected to, and aligned with, a Multi-branch optical fibre (9) so that any or all of the lasers can illuminate the sample (2). The common end of the Multi-branch optical fibre terminates in an optical system (10) which collimates the emerging light. This optical system is aligned with a beam expander 911) which matches the laser beam's diameter to that required by the microscope objectives (34,35) above the sample (2). The expanded beam then passes through an apodization plate (12) which distributes the optical energy evenly over the beam area.

The expanded and apodized beam is reflected by a beam splitter (31) and passes to the microscope objectives (34 and 35). The beam is focused by a microscope objective (34 or 35) on to the sample. In the micro mode this objective is selected to focus the beam to a diffraction limited spot size. A rotating turret (36), operated by an indexing mechanism (32), permits the objective to be changed for the macro mode where a larger area of the sample can be illuminated. In a further embodiment the apodization plate (12) can be removed so that the spot for the micro mode can be made smaller to allow higher injection levels.

An optical displacement sensor (38) measures the distance to the sample and, by means of a feedback loop through the antifocus controller (30), maintains the correct spacing by means of the piezo actuated focusing stage (33).

The Photoluminescence signal from the sample is collected by the microscope objective (34) (in the micro mode) and transported back through the beamsplitter (31) and a notch filter in the filter wheel (13) which contains notch filters matched to the range of laser wavelengths. The notch filter removes any reflected laser light, passing only the Photoluminescence signal.

The folding mirror (14) is swung out of the beam allowing the signal to pass to the tube lens (37), which may be incorporated to compensate for any infinity microscope objectives which may be used, and on to the cold mirror (17). This component reflects those wavelengths below a selected cut off point (approximately 700 nm) to the focusing lens (24) which focuses the signal into the detector (25). A filter wheel (23) in front of the detector focusing lens (24) contains filters to isolate selected wavelength bands.

The portion of the Photoluminescence signal lying in the wavelength range above the cut-off point passes through the cold mirror (17) and is similarly focused by the lens (22) into the detector (21). This signal also passes through a filter wheel (18) containing filters to isolate selected wavelength bands.

A series of pinholes of different diameters are contained in an aperture wheel (19) positioned in front of the detector (21). This aperture wheel can be moved axially by the piezo actuator (20) so that the pinholes can be positioned confocally with the desired image plane. By this means, planes at different depths in the sample (2) can be imaged to provide accurate depths information.

The electrical signal from the detectors (21,25) is fed to the lock-in amplifier (26) where it is synchronised with the modulation frequency of the laser (3–8) by means of a reference signal from the frequency generator (15). The electric signal is then fed to the central processor (40) for analysis. The PL image is obtained by raster scanning the stage. Alternatively optical scanning using galvo mirrors may be employed.

In an alternative micro mode of operation, the folding mirror (14) is swung into the beam of the Photoluminescence signal. The diverted signal passes through a filter wheel (27), which contains filters to isolate selected wavelength bands, and into the zoom lens (28). The zoom lens allows different magnifications to be used in imaging the illuminated spot on the sample (2) on to the CCD two dimensional array (29). This allows the illuminated area of the sample (2) to be imaged at different resolutions. The electrical signal from the CCD array is fed to the central processor (40) for analysis.

Using the aforedescribed apparatus of the invention investigations were undertaken in order to visualise defects in semiconductors and the results of these investigations are shown in FIGS. 1–8. The images are unique and cannot be obtained by any other method at room temperature. Generally, it can be seen that use of the equipment enables localisation and characterisation of defects in semiconductors. This enables one to more efficiently screen wafers for device fabrication and so safeguard against the production of defective semiconductors.

It can therefore be seen that the invention provides an apparatus and a method for imaging defects in a semiconductor or silicon structure which enables the defects to be imaged so that the density and spatial distribution of same can be determined.

The invention claimed is:

1. A method for identifying defects in a silicon structure comprising exposing said silicon structure to at least one high intensity beam of light characterised by a spot size of between 0.1 mm–0.5 microns and a peak or average power density of between $10^4$–$10^9$ watts/cm$^2$; and collecting luminescence from the silicon structure so as to visualize and observe defects in same by production of an image, characterized in that non-radiative recombination of electron pairs is detected as darkened regions in the image at the physical point of the defect.

2. A method according to claim 1 comprising selecting the wavelength of said light so as to identify defects at a selective depth in said silicon structure.

3. A method according to claim 1 wherein the high intensity beam of light is pulsed.

4. A method according to claim 1 comprising collecting luminescence from a series of focal planes.

5. An apparatus for undertaking photoluminescence imaging of a silicon structure characterised in that it comprises at least one high intensity light generating means which produces a beam of light having a spot size between 0.1 mm–0.5 microns and a peak or average power density of between $10^4$–$10^9$ watts/cm$^2$; a means for collecting luminescence from the silicon structure and means for producing photoluminescence images of said silicon structure in the form of an image so as to visualize and observe any defects that may be present, characterized in that means for collecting photoluminescence enable detection of non-radiative recombination of electron pairs, as darkened regions in the image at the physical point of the defect.

6. An apparatus according to claim 5 wherein said light generating means is provided with modulation means whereby the wavelength of said light beam can be selected.

7. An apparatus according to claim 5 wherein said light generating means is provided with modulation means whereby the intensity of said light beam is selected.

8. Apparatus according to claim 5 wherein means is provided to enable the high intensity beam of light to be pulsed.

9. Apparatus according to claim 5 wherein said light generating means is provided with modulation means whereby the frequency of said light beam is selected.

10. Apparatus according to claim 5 wherein said apparatus comprises confocal optics whereby images of said silicon structure is obtained through a series of focal planes.

11. A method for identifying defects in a semiconductor other than a silicon structure (non-silicon semiconductor) comprising exposing said semiconductor to at least one high intensity beam of light characterized by a spot size of between 0.1 mm–0.5 microns and a peak or average power density of between $10^4$–$10^9$ watts/cm$^2$; and collecting luminescence from the semiconductor so as to visualize and observe defects in same by production of an image, characterized in that non-radiative recombination of electron pairs is detected as darkened regions in the image at the physical position of the defect.

12. A method according to claim 11 comprising selecting the wavelength of said light so as to identify defects at a selective depth in said semiconductor.

13. A method according to claim 11 wherein the high intensity beam of light is pulsed.

14. A method according to claim 11 comprising collecting luminescence from a series of focal planes.

15. An apparatus for undertaking photoluminescence imaging of a semiconductor other than a silicon structure (non-silicon semiconductor) characterised in that it comprises at least one high intensity light generating means which produces a beam of light having a spot size between 0.1 mm–0.5 microns and a peak or average power density of between $10^4$–$10^9$ watts/cm$^2$; a means for collecting luminescence from said semiconductor, and means for producing photoluminescence images of said semiconductor in the form of an image so as to visualize and observe any defects that may be present, characterized in that means for collecting photoluminescence enable detection of non-radiative recombination of electron pairs, as darkened regions in the image at the physical point of the defect.

16. An apparatus according to claim 15 wherein said light generating means is provided with modulation means whereby the wavelength of said light beam can be selected.

17. An apparatus according to claim 15 wherein said light generating means is provided with modulation means whereby the intensity of said light beam is selected.

18. An apparatus according to claim 15 wherein means is provided to enable the high intensity beam of light to be pulsed.

19. An apparatus according to claim 15 wherein said light generating means is provided with modulation means whereby the frequency of said light beam is selected.

20. An apparatus according to claim 15 wherein said apparatus comprises confocal optics whereby images of said semiconductor is obtained through a series of focal planes.

* * * * *